(12) United States Patent
Yuhara et al.

(10) Patent No.: US 6,310,356 B1
(45) Date of Patent: Oct. 30, 2001

(54) FLUID FINE PARTICLE MEASURING SYSTEM FOR PROCESSING SEMICONDUCTORS

(75) Inventors: Yoshihito Yuhara; Riichiro Suzuki, both of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/251,649

(22) Filed: Feb. 17, 1999

(30) Foreign Application Priority Data

Feb. 18, 1998 (JP) .................................................. 10-054413
Feb. 16, 1999 (JP) .................................................. 11-037049

(51) Int. Cl.7 ............................ G01N 15/14; G01B 11/00
(52) U.S. Cl. ........................................... 250/574; 356/338
(58) Field of Search ................................... 250/573, 574; 356/338, 339

(56) References Cited

U.S. PATENT DOCUMENTS 4,779,451 * 10/1988 Ezawa et al. ....................... 73/53.01

FOREIGN PATENT DOCUMENTS 61181939   8/1986   (JP) .
8145856    6/1996   (JP) .

* cited by examiner

*Primary Examiner*—F. L. Evans
(74) *Attorney, Agent, or Firm*—Price and Gess

(57) ABSTRACT

A fine particle measuring system for semiconductor cleaning fluid includes a sample tank for holding a sample of the cleaning fluid and a pump that can circulate the sample of cleaning fluid. A return conduit is connected to a filter and a bubble discharge opening member to return a major portion of the sample of cleaning fluid to the sample tank. A minor portion of the cleaning fluid is directed respectively to a cooling unit, and then to a deaerator for eliminating any effects of bubbles on the measurement of fine particles in the cleaning fluid. A first conduit is connected to a measuring cell to return the sample cleaning fluid to the sample tank while a second conduit is connected to the deaerator to draw gas from the bubbles that have been separated from the deaerator.

20 Claims, 3 Drawing Sheets

FLUID FINE PARTICLE MEASURING SYSTEM FOR PROCESSING SEMICONDUCTORS

BACKGROUND OF THE INVENTION

1. Field of the Invention

The present invention relates to a fluid fine particle measuring system and more particularly to a particle measuring system capable of measuring the fine particles contained in a cleaning liquid used for cleaning a silicone wafer in the process of producing semiconductors.

2. Description of Related Art

During the production of semiconductors, a substantial amount of cleaning fluid is required and it is necessary to monitor the purity of the cleaning fluid by measuring the number of fine particles that can be accumulated as a result of the cleaning action. Generally, a predetermined number of fine particles is set and if the cleaning fluid exceeds that number it cannot be used in the process of making semiconductors.

Thus, it is important to insure a precise technique of measuring the fine particles contained in the cleaning fluid. The prior art has used a technique wherein a portion of the cleaning fluid is introduced as sample fluid into a flow-type measuring cell, and a laser beam from a laser light source is emitted into the fluid as an incident light, and the resulting scattered light that can be generated from the fine particles that are suspended in the sample fluid is then measured by a photodetector so that both the size and number of fine particles in the sample fluid are measured.

The cleaning fluid that is frequently utilized in cleaning silicone wafers is a chemical solution which is prepared by mixing ammonia water, hydrogen peroxide water and pure water in a suitable ratio. An alternative cleaning fluid can be prepared by mixing hydrochloric acid, hydrogen peroxide water and pure water in a suitable ratio. Both of these examples of cleaning fluids are prone to froth when used for a cleaning purpose and bubbles are then easily produced in the cleaning fluid and can be introduced into the flow channel of the measuring cell. The presence of bubbles within the sample fluid supplied to the measuring cell can be misdetected as fine particles and thus an error can appear in the measured results resulting in an excessive wastage in the cleaning fluid or an interruption in the process of producing semiconductors.

One technique for eliminating bubbles produced in a sample fluid, in a flow channel of a measuring cell, has been suggested in the Japanese Patent Application Laid-Open No. 61-181939 (1986). In this submerged fine particle measuring system an electronic cooler, for cooling the sample fluid by 10° C.–15° C. cooler than the temperature at the time of the measuring cycle, is provided in combination with a deaerator for reducing the normal pressure, so as to thereby eliminate any bubbles that are provided in the flow channel. The electronic cooler and the deaerator are provided on an upper stream side of the measuring cell. A problem exists, however, in that the pressure may not eliminate larger bubbles contained in the sample fluid and thus there is a possibility that a growth of bubbles can be encouraged in the measuring cell.

In addition, the submerged fine particle measuring system disclosed in the 61-181939 reference requires an active deaerator to provide a reduced pressure to eliminate the bubbles through the use of a vacuum pump. Thus, the cost of such a deaerator system becomes a factor and an increase in space is required adjacent the gas stick.

The semiconductor industry is still attempting to minimize the amount of space that is used for semiconductor tools while increasing the efficiency of monitoring the status of a cleaning fluid.

SUMMARY OF THE INVENTION

The present invention provides a compact structure for a submerged fine particle measuring system wherein bubbles that are produced in the sample fluid can be eliminated at a relatively low cost while maintaining high accuracy.

The present invention utilizes a submerged fine particle measuring system where light is emitted into a measuring cell containing sample fluid flowing through the measuring cell. The scattered light generated from fine particles contained in the sample fluid is detected by an optical detector and a number of fine particles can be counted based on the output of the optical detector.

A cooling unit for cooling the sample fluid so as to dissolve bubbles that may be mixed in the sample fluid is provided, along with a deaerator for separating and eliminating the bubbles in the sample fluid on the upstream side of the measuring cell. The deaerator is passive and is connected with an exhaust line which can be connected to the return line from the sample cell, so that a bubble discharge opening provided in the upper portion of the deaerator is connected through the return line to the lower stream side of the measuring cell.

In the submerged fine particle measuring system of the present invention the solubility of bubbles in the sampling fluid is increased by the cooling unit, so that bubbles cannot be recognized visually and are dissolved within the sample fluid. Additionally, bubbles which may grow downstream of the cooling unit are appropriately separated by the aerator tank, with the gas bubbles drawn off and discharged into a downstream side of the sampling cell, so that the cleaning fluid with the bubbles are discharge or are reintroduced into a storage tank.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may be best understood by reference to the following description taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a system for measuring fine particles in cleaning fluid.

Figure 1:
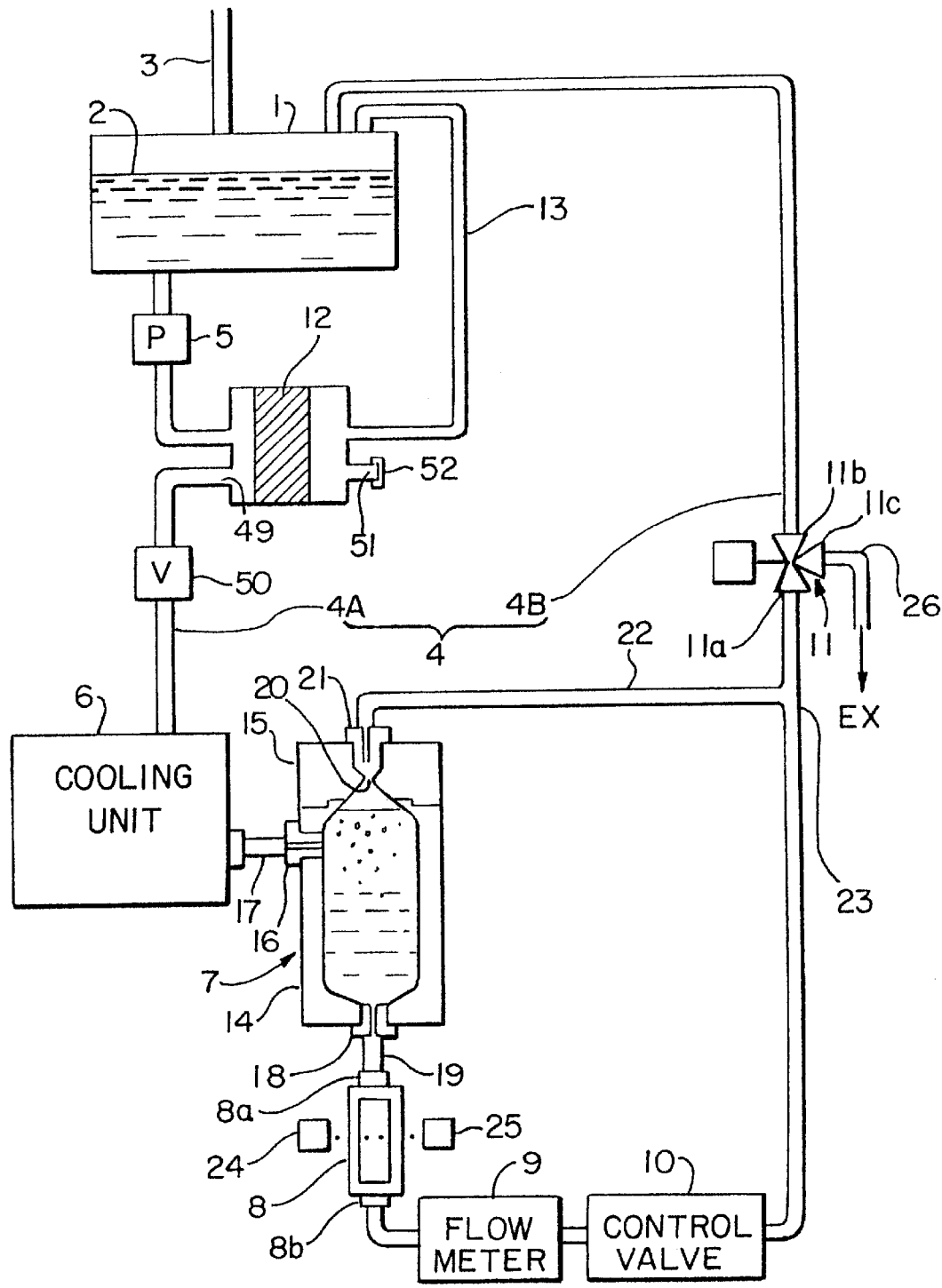
FIG. 1 is a schematic drawing showing a submerged fine particle measuring system to a first embodiment of the present invention.

Referring to FIG. 1, a schematic illustration showing a submerged fine particle measuring system of a first embodiment of the present invention is disclosed. A sample tank 1 houses the sample fluid 2. Cleaning fluid is introduced through a pipe or tube 3 so that a portion of the cleaning fluid, through a cleaning line not shown, can be drawn off as a sample fluid 2 to be supplied to the overflow tank or sample tank 1. A conduit, or flow channel 4 for circulating and supplying the sample fluid 2 and the sample tank 1 to a measuring cell 8 is utilized. A control valve 50 can be opened automatically by a computer control measuring cycle to provide access to the measuring cell 8. A flow channel in the upper stream side coming from the sample tank 1 to the measuring cell 8 is represented by the reference code 4a, while a flow channel in the lower stream side from the measuring cell 8 to return the fluid to the sample tank 1 is represented by the reference code 4b.

As fluid is drawn off from the sample tank 1 by a pump 5, the fluid is introduced if the control valve 50 is open to a cooling unit 6 and then subsequently in series to a passive deaerator 7. The filter 12 also includes a bubble discharge opening 51 and a cap 52 to eliminate gas. When the valve 50 is open, a low flow rate bypasses the filter 12 and goes directly to the cooler unit 6 while a higher flow rate passes through the filter 12 to be returned to the sample tank 1.

The deaerator 7, in turn, is connected to the entrance port or introduction opening 8a of the measuring cell 8. Downstream of the measuring cell 8 is a flow meter 9, a control valve 10 and a switching valve 11. The lower stream side 4b is connected to the sample tank 1 or to a discharge line not shown by a valve 11.

The pump 5 can consist of a pressed feeding type pump and is connected with the sample tank, via a return flow channel 13. One portion of the sample fluid 2 introduced from the sample tank 1 passes through the pump 5, the filter 12 and the return flow channel 13, so as to be returned to the sample tank 1. Another portion of the sample fluid 2 is sent from the pump 5 to the cooling unit 6. The pump 5 basically controls the flow of the sample fluid throughout the entire measuring system or cleaning unit and can be controlled by an arithmetic and control unit, such as a computer or microcomputer that is appropriately programmed for performing the cleaning cycle and the measurement cycle of the cleaning fluid.

The cooling unit 6 cools the sample fluid 2 so as to dissolve bubbles that may be mixed in the sample fluid 2. The cooling unit 6 can be an electronic cooler that can use a Peltier element as its active member although other elements for cooling can be used.

A passive deaerator 7 separates and eliminates bubbles that are mixed in the sample fluid 2 as the sample fluid flows, from the cooling unit 6 through the conduit 17, to an introduction plug 16 on the upper portion of the side wall of the unit main body 14, of the deaerator 7. The unit main body 14 is formed in a cylindrical shape and has a top cover 15 that seals the upper opening of the unit main body 14. The unit main body 14 and the top cover 15 are fastened together, so that they are both air-tight and liquid tight to each other via a sealing member not shown by using a suitable mounting structure.

The introduction plug 16 is provided on the upper portion of the side wall of the unit main body 14. An exit plug 18, for permitting the sample fluid to be released on the bottom portion of the unit main body 14, is connected with a flow channel 19 that leads the bubble-free sample fluid to the introduction opening 8a of the measuring cell 8.

The structure of the top cover 15 is formed so that the inner surface has a funnel-like shape facing upward, and further includes a bubble or gas discharge opening 20 having a pin-hole shape, for example, a diameter of about 0.2 mm with an opening at the central portion of the top part of the top cover 15. A connection plug 21 is provided above the opening 20 and is connected with a bubble discharge flow channel 22. The lower stream side of the bubble discharge flow channel 22 is connected with a point 23, between the control valve 10 and the switching valve 11, on the flow channel 4b so as to thereby bypass the measuring cell 8, the flow meter 9 and the control valve 10.

The measuring cell 8 is of the so-called flow type and is not shown in detail since its operation is known in the art. The measuring cell 8 has a main body of a rectangular parallelepiped shape, with an introduction opening 8a formed at one end in a longitudinal direction, and a leading-out opening 8b is formed at the other end.

Optical transmission windows are provided on, respectively, the right and left side surface of the measuring cell 8 and they are arranged perpendicular to a light path from a laser light source 24 on one side, which emits a laser beam to the sample fluid 2 in the measuring cell 8, while a photodetector 25 is mounted on the other side of the optical transmission window to detect scattered light produced in measuring cell 8, when the laser beam contacts any suspended particles in the sample fluid. An output signal of the photodetector 25 can be inputted into an arithmetic control unit, such as a personal computer for measuring the fine particles in accordance with an algorithm known in the art.

The flow meter 9 can measure the flow rate of the sample fluid 2 flowing in the measuring cell 8 while the control valve 10 can regulate the flow rate of the sample fluid 2 flowing through the measuring cell 8. By knowing the flow rate and the output of the photodetector 25, it is possible to calculate the quantity of fine particles in a volume of the cleaning fluid.

The switching valve 11 in the downstream flow channel 4b can comprise a three-way solenoid valve which can also be controlled by the computer. In this regard, its first port 11a and its second port 11b are connected with the flow channel 4b, while a third port 11c is connected with a drain flow channel 26. Generally, in a measurement cycle the first port 11a and the second port 11b are normally interconnected with each other.

In the operation of the submerged fine particle measuring system of the present invention, one portion of the sample fluid 2, that is withdrawn from the sample tank 1, is fed by the pump 5 to the cooling unit 6 when the valve 50 is opened. The other portion is directed through the return flow channel 13 to the filter 12 for filtering. The portion of the sample fluid 2 that is directed to the cooling unit 6 may contain small bubbles which cannot be recognized visually and slightly larger bubbles, which have grown in flow channel 14, are intermixed in the sample fluid 2. The cooling unit 6 cools the fluid so that the solubility of the bubbles is increased in the cleaning fluid. As a result, the very small bubbles which are contained are rendered visually invisible or are dissolved in the sample fluid 2, while new large bubbles are not produced. Since the sample fluid 2 is cooled in the cooler unit 6, so that the solubility of the bubbles is increased, it is preferable that the distance between an exit of the cooling unit 6 and the entrance 8a of the measuring cell 8 is set to be as short as possible, so that the temperature of the sample fluid 2 cooled by the cooling unit 6 does not rise in the interim. As a result, the further production of bubbles in sample fluid 2 can be suppressed between the cooling unit 6 and the measuring cell 8.

The cooled sample fluid 2 is introduced into a passive deaerator 7 and bubbles contained within this fluid can rise within the chamber and eventually pass through a bubble leading-out opening 20 within the plug 21, they are discharged into the bubble discharged flow channel 22 so that comparatively large bubbles in the sample fluid 2 that may impact upon the measurement cycle are eliminated. The bubble discharge flow channel 22 is connected to the discharge channel 23 from the measuring cell 8. While not shown, a check valve can be inserted within the bubble discharge channel 22 to prevent any backflow into the deaerator 7. The relative size of the bubble discharge flow channel 22 and the discharge flow channel 23 is such that the velocity of fluid flow across the opening of the bubble discharge channel 22, into the flow channel 23, can create a negative pressure state to assist in drawing the gas for intermixing with the fluid in the flow channel 23. The pressure from the pump 5 and the control valve 10 is great and when the control valve 10 and the valve 50 are open the fluid flow creates a pressure differential that is known in the art.

Therefore, when the sample fluid 2 which is passed through the cooling unit 6 and the deaerator 7, reaches the measuring cell 8, almost all bubbles are eliminated from the sample fluid 2. The resulting measurement by the illumination of the laser light from the source 24, and the measurement of the resulting scattered light by the optical detector 25, can provide a highly accurate reading of the existence of fine particles in the cleaning fluid. As a result, the size and number of fine particles contained in the sampling fluid 2 are obtained. When the sample fluid 2 exits the measuring cell 8, it passes through the flow meter 9, the control valve 10, and then the switching valve 11, and joins with the discharge from the bubble discharging flow channel 22. The resulting mixture is returned to the sample tank 1 via the switching valve 11 and the flow channel 4b. The first port 11a and the third port 11c are interconnected with each other by the operation of the switching valve 11, so that the sample fluid 2 from the measuring cell 8 and the bubbles flowing in the bubble discharge flow channel 22 may be discharged into the drain flow channel 26.

Referring to the deaerator 7, since the bubble discharge opening 20 is formed in to a pinhole shape, it is somewhat difficult for a liquid to pass through this shape, but the gas can be easily passed there through and therefore eliminated from the deaerator 7. In the example of a chemical cleaning fluid where a significant amount of bubbles can be generated, this arrangement can efficiently eliminate the bubbles prior to the measurement cycle. In the deaerator 7, the bubbles are separated from the sample fluid 2 by an ascending force and a vacuum pump is not necessary, thereby permitting the deaerator chamber to be compact and the relative cost of this measuring system to be reduced.

Figure 2:
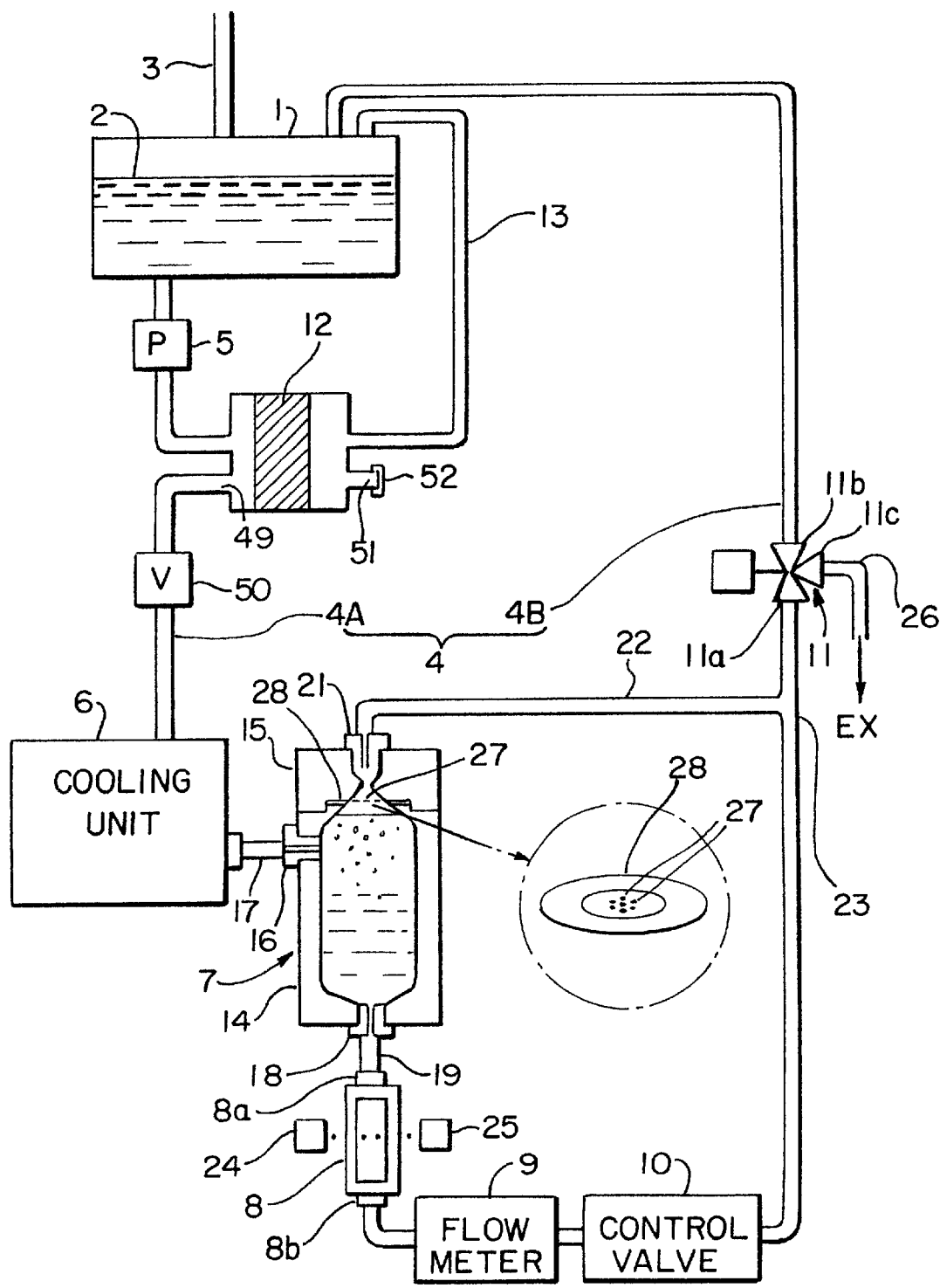
FIG. 2 is a schematic drawing showing a submerged fine particle measuring system according to a second embodiment of the present invention.

FIG. 2 is a schematic drawing of a second embodiment of the present invention. In this embodiment, the deaerator 7 has a partition plate 28 in which a plurality of fine holes, which act as bubble discharge openings 27, are provided on the top cover 15 as shown in the enlarged portion of the drawing. In this embodiment, the total sum of the cross sections of the plurality of fine holes 27 is set, so as to be equal with the cross section of the flow channel in the plug 21 that is about 0.0317 $mm^2$. The operation of the second embodiment remains the same as that of the first embodiment and, accordingly, will not be repeated herein.

Figure 3:
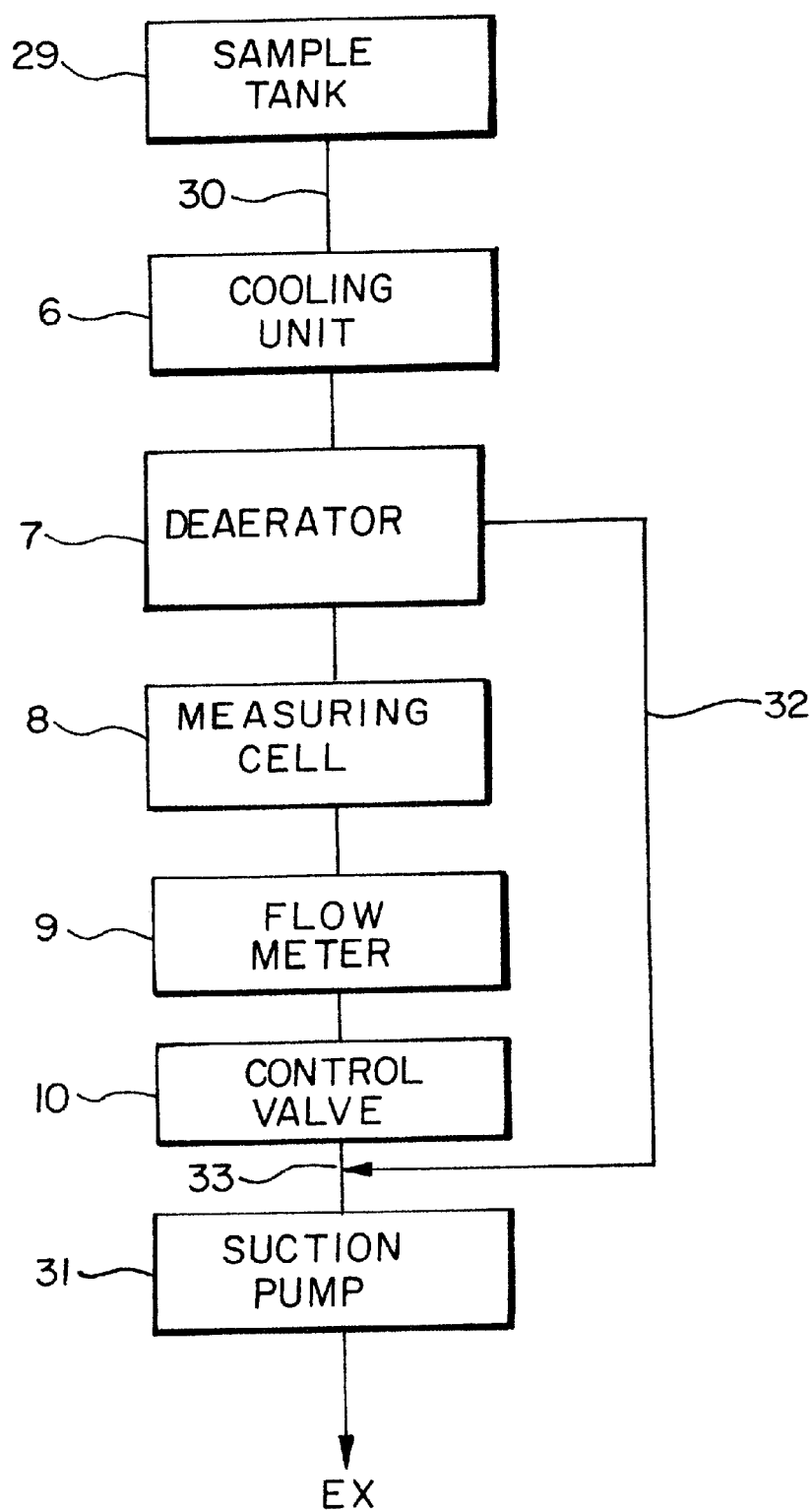
FIG. 3 is a schematic drawing showing a submerged fine particle measuring system according a third embodiment of the present invention.

In each of the embodiments herein, the pressurizing pump 5 acts as a pressurizing source of pump means for the cleaning fluid, but the system may use a suction sampler instead of the pressurizing source to provide for liquid flow through the measuring cell 8. Referring to FIG. 3, a schematic drawing shows a third embodiment of the present invention. In FIG. 3, the sample tank 29, the cooling units 6, the deaerator 7, the measuring cell 8, the flow meter 9 and the control valve 10 have the same constitution as in the earlier embodiments and are provided in this order on a flow channel 30 on the lower stream side of the sample tank.

In addition, a suction pump 31 can act as the suction sampler and is provided in the lower stream side of the control valve 10. The lower stream side of the suction pump 31 is connected with the drain flow channel which is not shown. The conduit 32 is the bubble discharge flow channel which is connected between the deaerator 7 and its lower stream side to a point 33 between the control valve 10 and the suction pump 31 on the flow channel 30. This third embodiment produces the same effect as the other embodiments and is particularly suitable in the case where a sample fluid 2 can consist of pure water.

The present invention is not limited to the above-mentioned embodiments and various modifications can be incorporated. For example, the cooling unit 6 and the deaerator 7 may be provided in the previous stage of the measuring cell 8 and in positions closest to the measuring cell 8, and the cooling unit 6 may be positioned in the lower stream side of the deaerator 7. Additionally, other forms of cooling units then an electronic cooler can be used as the cooling unit 6. The lower stream sides of the bubble discharge flow channels 22, 32 may be connected with the flow channel between the flow meter 9 and the control valve 10. In addition, a mass flow controller which is constituted so that a flow rate measuring section and a flow rate control valve are united in one body can be provided instead of providing a separate flow meter 9 and a separate control valve 10.

According to the submerged fine particle measuring system of the present invention, even when bubbles are produced in a sample fluid such as a cleaning fluid for use in the semiconductor industry they can be eliminated so that they do not affect the measuring cycle that takes place in the measuring cell. As a result, high accuracy measurements can be taken to insure the accuracy of the semiconductor processing procedures. Additionally, the submerged fine particle measuring system of the present invention can be relatively compact and thereby save installation space while being relatively economical.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. In a fine particle measuring system for liquids wherein light is directed through a measuring cell containing a sample of liquid and a detector system measures the light from the measuring cell to determine a measurement of the fine particles, the improvement comprising:

a cooling unit to cool the sample liquid before entering the measuring cell;

a deaerator for separating gas bubbles from the sample liquid before entering the measuring cell;

a first conduit connected to the measuring cell to receive the sample liquid as it is exhausted from the measuring cell; and a second conduit connected between the deaerator and the first conduit to draw the gas from the bubbles separated from the deaerator and to mix the gas with the exhausted sample liquid.

2. The fine particle measuring system of claim 1 wherein the deaerator is passive and relies only on the second conduit connection to remove the gas from the bubbles.

3. The fine particle measuring system of claim 1 wherein a bubble discharging opening of a restricted configuration is positioned at an upper portion of the deaerator and connected to the second conduit.

4. The fine particle measuring system of claim 3 wherein the bubble discharge opening has an aperture of approximately 0.2 mm.

5. The fine particle measuring system of claim 3 wherein the bubble discharge opening includes a partition plate with a plurality of small holes.

6. The fine particle measuring system of claim 5 wherein the area of the small holes is approximately 0.0317 mm$^2$.

7. The fine particle measuring system of claim 1 further including a pump connected upstream of the measuring cell to provide a positive pressure of sample liquid.

8. The fine particle measuring system of claim 1 further including a suction pump connected downstream of the measuring cell to draw the sample liquid through the measuring cell.

9. The fine particle measuring system of claim 1 further including a flow meter unit and a control valve mounted to the first conduit.

10. The fine particle measuring system of claim 1 wherein the relative size of the second conduit to the first conduit is such to create a negative pressure in the second conduit when sample fluid is forced through the first conduit.

11. The fine particle measuring system of claim 1 where the cooling unit includes a Peltier element to cool the sample liquid.

12. A fine particle measuring system for semiconductor cleaning fluid, wherein light is directed through a measuring cell containing a sample of cleaning fluid and a detector system measures the light from the measuring cell to determine a measurement of the fine particles in the cleaning fluid, comprising:

means for circulating the sample of cleaning fluid;

a cooling unit to cool the sample cleaning fluid before entering the measuring cell;

a deaerator for removing gas bubbles from the sample cleaning fluid;

a first conduit connected to the measuring cell to receive the sample cleaning fluid as it is exhausted from the measuring cell; and a second conduit connected to the deaerator and the first conduit to draw the gas from the bubbles separated from the deaerator and to mix the gas with the exhausted sample cleaning fluid, the means for circulating forcing the exhausted sample cleaning fluid in the first conduit past the second conduit connection to provide a negative pressure to draw the gas from the deaerator into the exhausted sample cleaning fluid in the first conduit.

13. The fine particle measuring system of claim 12 wherein the deaerator is passive and relies only on the second conduit connection to remove the gas from the bubbles.

14. The fine particle measuring system of claim 12 wherein a bubble discharging opening of a restricted configuration is positioned at an upper portion of the deaerator and connected to the second conduit.

15. The fine particle measuring system of claim 14 wherein the bubble discharge opening has an aperture of approximately 0.2 mm.

16. The fine particle measuring system of claim 14 wherein the bubble discharge opening includes a partition plate with a plurality of small holes.

17. A fine particle measuring system for semiconductor cleaning fluid, wherein light is directed through a measuring cell containing a sample of cleaning fluid and a detector system measures the light from the measuring cell to determine a measurement of the fine particles in the cleaning fluid, comprising:

a sample tank for holding a sample of cleaning fluid;

pump means for circulating the sample of cleaning fluid;

a return conduit connected to the sample tank and to the pump means including a filter and a bubble discharge opening member connected to the filter;

a cooling unit to cool the sample cleaning fluid before entering the measuring cell, the pump means directs a major portion of the cleaning fluid to the filter and a minor portion to the cooling unit;

a deaerator connected to the cooling unit and the measuring cell for removing gas bubbles from the sample cleaning fluid;

a first conduit connected to the measuring cell to receive the sample cleaning fluid as it is exhausted from the measuring cell; and a second conduit connected to the deaerator and the first conduit to draw the gas from the bubbles separated from the deaerator and to mix the gas with the exhausted sample cleaning fluid, the pump means for circulating forcing the exhausted sample cleaning fluid in the first conduit past the second conduit connection to provide a negative pressure to draw the gas from the deaerator into the exhausted sample cleaning fluid in the first conduit.

18. The fine particle measuring system of claim 17 where the cooling unit includes a Peltier element to cool the sample cleaning fluid.

19. The fine particle measuring system of claim 17 wherein the pump means includes a pump connected upstream of the measuring cell to provide a positive pressure of sample cleaning fluid.

20. The fine particle measuring system of claim 17 wherein the pump means includes a suction pump connected downstream of the measuring cell to draw the sample cleaning fluid through the measuring cell.

* * * * *